(12) United States Patent
Cheng

(10) Patent No.: US 8,974,528 B2
(45) Date of Patent: Mar. 10, 2015

(54) SPINE REPLACEMENT SYSTEM FOR THE TREATMENT OF SPINE INSTABILITY AND DEGENERATIVE DISC DISEASE

(75) Inventor: David Ming Cheng, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1827 days.

(21) Appl. No.: 10/569,437

(22) PCT Filed: Oct. 5, 2004

(86) PCT No.: PCT/US2004/032874
§ 371 (c)(1),
(2), (4) Date: Oct. 16, 2006

(87) PCT Pub. No.: WO2005/034864
PCT Pub. Date: Apr. 21, 2005

(65) Prior Publication Data
US 2007/0093903 A1    Apr. 26, 2007

Related U.S. Application Data

(60) Provisional application No. 60/509,604, filed on Oct. 8, 2003.

(51) Int. Cl.
*A61F 2/44* (2006.01)
*A61B 17/70* (2006.01)
(Continued)

(52) U.S. Cl.
CPC . *A61F 2/44* (2013.01); *A61F 2/441* (2013.01); *A61B 17/7059* (2013.01); *A61F 2/442* (2013.01); *A61F 2/4455* (2013.01); *A61F 2/4611* (2013.01); *A61F 2002/2817* (2013.01); *A61F 2002/2835* (2013.01); *A61F 2002/30383* (2013.01); *A61F 2002/30507* (2013.01); *A61F 2002/30517* (2013.01); *A61F 2002/30586* (2013.01); *A61F 2002/30599* (2013.01);
(Continued)

(58) Field of Classification Search
USPC .............................................. 623/17.11–17.16
See application file for complete search history.

(56) References Cited

U.S. PATENT DOCUMENTS

| | | | |
|---|---|---|---|
| 5,458,642 A | 10/1995 | Beer | |
| 6,001,130 A * | 12/1999 | Bryan et al. | ............... 623/17.16 |

(Continued)

OTHER PUBLICATIONS

International Search Report and Notification of Transmittal with Written Opinion dated May 2, 2005.
(Continued)

*Primary Examiner* — Bruce E Snow
(74) *Attorney, Agent, or Firm* — Jenkins, Wilson, Taylor & Hunt, P.A.

(57) ABSTRACT

Apparatuses and methods for single disc arthroplasty and multi-segmental spine replacement recreating the anterior and middle columns of the subaxial spine complete with adjacent motion segments are disclosed. The surgical implant assembly includes a first cage adapted to be rigidly attached to a first vertebra, a second cage adapted to be rigidly attached to a second vertebra, and a spinal disc replacement prosthesis positioned between the first and second cages. The spinal disc replacement prosthesis preferably includes a resilient plastic or elastomeric body having two or more adjustably fluid-filled compartments therein, the fluid-filled compartments each being adjustably fluid filled by a respective port defined in the prosthesis body.

34 Claims, 10 Drawing Sheets

(51) Int. Cl.
- *A61F 2/46* (2006.01)
- *A61F 2/28* (2006.01)
- *A61F 2/30* (2006.01)

(52) U.S. Cl.
CPC ............... *A61F 2002/30785* (2013.01); *A61F 2002/30892* (2013.01); *A61F 2002/449* (2013.01); *A61F 2220/0025* (2013.01); *A61F 2250/0063* (2013.01)
USPC ..................................................... 623/17.12

(56) References Cited

U.S. PATENT DOCUMENTS

| | | | |
|---|---|---|---|
| 6,156,067 A * | 12/2000 | Bryan et al. | 623/17.15 |
| 6,419,704 B1 | 7/2002 | Ferree | |
| 6,733,533 B1 | 5/2004 | Lozier | |
| 6,827,740 B1 * | 12/2004 | Michelson | 623/17.11 |
| 7,077,865 B2 * | 7/2006 | Bao et al. | 623/17.12 |
| 7,291,150 B2 * | 11/2007 | Graf | 606/86 A |
| 7,731,753 B2 * | 6/2010 | Reo et al. | 623/17.13 |
| 2002/0183848 A1 | 12/2002 | Ray et al. | |
| 2004/0193273 A1 | 9/2004 | Huang | |
| 2004/0260396 A1 | 12/2004 | Ferree et al. | |
| 2005/0060034 A1 | 3/2005 | Berry et al. | |

OTHER PUBLICATIONS

Lunsford et al., "Anterior surgery for cervical disc disease," J Neurosurg, vol. 53, pp. 1-11 (1980).

Denis, "The Three Column Spine and Its Significance in the Classification of Acute Thoracolumbar Spinal Injuries," Spine, vol. 8, No. 8, pp. 817-831 (1983).

Gore et al., "Anterior Cervical Fusion for Degenerated or Protruded Discs," Spine, vol. 9, No. 7, pp. 667-671 (1983).

Clements et al., "Anterior Cervical Discectomy and Fusion," Hospital for Special Surgery, vol. 15, No. 10, pp. 1023-1025 (1990).

Baba et al., "Late Radiographic Findings After Anterior Cervical Fusion for Spondylotic Myeloradiculopathy," Spine, vol. 18, No. 15, pp. 2167-2173 (1993).

Enker et al., "Artificial Disc Replacement," Spine, vol. 18, No. 8, pp. 1061-1070 (1993).

Griffit et al., "A Multicenter Retrospective Study of the Clinical Results of the LINK SB Charite Intervertebral Prothesis," Spine, vol. 19, No. 16, pp. 1842-1849 (1994).

University of Modena, Italy, "Results of disc prothesis after a minimum Spine 21," Wolters Kluwer Health, vol. 2, pp. 995-1000 (1996).

Hilibrand et al., "The Success of Anterior Cervical Arthrodesis Adjacent to a Previous Fusion," Spine, vol. 22, No. 14, pp. 1574-1579 (1997).

Hilibrand et al., "Radiculopathy and Myelopathy at Segments Adjacent to the Site of a Previous Anterior Cervical Arthrodesis," The Journal of Bone and Joint Surgery, Incorporated, vol. 81, No. 4, pp. 519-528 (1999).

Zeegers et al., "Artificial disc replacement with the modular type SB Charite III: 2-year results in 50 prospectively studied patients," Eur Spine J, vol. 8, pp. 210-217 (1999).

DiAngelo et al., "Anterior Cervical Plating Reverses Load Transfer Through Multilevel Strut-Grafts," Spine, vol. 25, No. 7, pp. 783-795 (2000).

Goffin et al., "Preliminary Clinical Experience with the Bryan Cervical Disc Prosthesis," Rapid Communication, vol. 51, No. 3, pp. 840-847 (2002).

Wigfield et al., "Influence of an artificial cervical joint compared with fusion on adjacent-level motion in the treatment of degenerative cervical disc disease," Spine 1, vol. 96, pp. 17-21 (2002).

* cited by examiner

SPINE REPLACEMENT SYSTEM FOR THE TREATMENT OF SPINE INSTABILITY AND DEGENERATIVE DISC DISEASE

RELATED APPLICATIONS

This application claims the benefit of U.S. Provisional Patent Application Ser. No. 60/509,604, filed Oct. 8, 2003; the disclosure of which is incorporated herein by reference in its entirety.

TECHNICAL FIELD

The subject matter disclosed herein relates generally to prosthetic systems. More particularly, the present subject matter relates to apparatuses and methods for recreating the anterior and middle columns of the subaxial spine complete with adjacent motion segments.

BACKGROUND ART

The spinal column surrounds and protects the spinal cord and is a column made of up bones, discs and ligaments. The spinal column is made up of 24 bone segments (7 cervical, 12 thoradic, and 5 lumbar spinal vertebrae), plus the sacrum and the tailbone (coccyx), and provides the supporting structure of the spine. Nerves branch out from the spinal cord and pass through openings between the vertebrae to obtain sensation from and control the movements of our body parts.

Discs are located between the bone segments (vertebrae) and function as "shock absorbers" and give the spine flexibility to move and bend. The outer part of the disc is called the annulus fibrosus (annulus), which is a strong structure that surrounds and supports an inner jelly material called the nucleus pulposus (nucleus). Disc material in the nucleus is mainly composed of water and proteins (collagen) and as the body ages, the water content decreases as the collagen content increases. This causes the disc to be more susceptible to degeneration (or flattening) wherein the inner jelly material (nucleus) can bulge and press against the annulus fibrosus. This can stimulate pain receptors, causing pain to occur. With age, the disc is also more susceptible to injury such as tears in the annulus that can lead to a condition known as a herniated disc, wherein the nucleus of the disc escapes the annulus and may then press upon adjacent nerves or the spinal cord. If uncorrected, this disc herniation can lead to excruciating pain, deformity, and neurological and musculoskeletal dysfunction. While non-surgical options such as rest, heat, pain medications and physiotherapy are available to patients with disc degradation or injuries, these conditions sometimes require surgical intervention.

Of interest with respect to disc degradation or injuries, it should be understood that prior to the 1900's, treatment options for osteoarthritic degenerative joint disease, such as that of the hip and knee, were limited. Surgeons performed limited procedures to relieve terrible pain, including joint debridements, nerve division, osteotomy, and if all else failed, arthrodesis (fusion) of the diseased joint. While hip and knee fusion were successful in terms of pain relief from the diseased joints, it placed substantial non-physiologic strain on surrounding joints as well as the spine, typically in an individual already beset by degenerative joint disease. This resulted in a cascade of joint failures in both legs and hips, and further pain. In the 1960's, the advent of hip arthroplasty by Sir John Charnley and subsequent knee arthroplasty in the early 1970's ended the need for most patients to undergo such long bone arthrodesis, marking a substantial improvement in the quality of life surgeons could offer to patients with degenerative joint disease. But, while hip and knee procedures were improved, procedures for dealing with spine disorders have been slower in development by medical professionals.

Up until the last few years, anterior cervical discectomy and arthrodesis were the standard surgical methods for dealing with disc degradation or damaged vertebral bodies. In the cervical spine, anterior cervical discectomy involves the removal of the entire diseased spinal disc to relieve the lower back or leg pain associated therewith. The disc is replaced with a bone graft, and the entire complex of the graft and the adjacent vertebral bodies is then secured with a plate and screws, allowing the complex to then fuse over the ensuing months following the surgery. Unfortunately, this fusion of vertebral bodies result in redistributed spinal loading stresses and can accelerate degenerative processes in the cervical discs above and below.

Arthrodesis (or spinal fusion) is also performed to address other spine problems, such as vertebral body fractures or scoliosis. As shown in FIGS. 1A and 1B, when spinal fusion SF is performed, the second cervical vertebra V2 is removed (corpectomy), with discectomies performed above and below the resected vertebral body. A bone graft BG is then inserted into the void between the first V1 and third V3 vertebrae and a plate PL is positioned over first V1 and third V3 vertebrae and bone graft BG that lies in between. Screws SW are used to secure plate PL to first vertebra V1, intermediate bone graft BG, and third vertebra V3 so that the first and third vertebrae and bone graft are mechanically secured. With time, bone fusion will occur between the first vertebra, bone graft, and the third vertebrae, and the entire segment will act biomechanically as a single long bone segment.

While 50% to 94% of patients have good to excellent results immediately after arthrodesis, adjacent motion segment(s), specifically the intervertebral discs, are lost in this process. This results in a non-physiologic spine that distributes stress unevenly and results in greater wear and tear in adjacent segments. The remaining motion segments immediately above and below the long fusion mass experience a disproportionate degree of biomechanical stress, and are at greater risk of developing instability in turn, a condition also known as "adjacent segment disease". Studies indicate that up to 30% of patients who undergo single-level spine fusion require reoperation to treat disc degeneration at the next level either above or below the original fusion within ten years. It became evident that a need existed for a new system to treat spinal disease in a manner that avoids fusion of movement segments.

With knowledge of the disadvantages of spinal fusion and the advantages of hip and knee arthroplasty, it was inevitable that artificial hip and knee technology would be translated to artificial disc designs for spinal arthroplasty. Such research has proliferated over the last decade, with the development of multiple approved artificial disc designs in Europe.

When dealing with artificial disc concepts, those of skill in the art generally divide prosthetic discs into two major categories: nucleus replacements and total disc replacements.

Nucleus replacements are designed for use when the major feature of the degenerative process involves the nucleus pulposus but has spared the annulus and supporting structures. Consequently, nucleus replacement is useful only during the early stages of disc degeneration where minimal segment collapse has occurred. Nucleus replacement requires creating a hole in the annulus to insert the prosthetic nucleus. Since the prosthetic nucleus is unattached inside the annulus, it is sometimes expelled from the annulus through the hole.

An example of a nucleus replacement is the PROSTHETIC DISC NUCLEUS (available from Raymedica of Bloomington, Minn.) generally shown as PDN in FIG. 2A. PDN is an implant with a hydrogel core C wrapped in a woven polyethylene cover. A dehydrated spacer, it expands as it absorbs water after implantation. The size of the implant varies and it can be placed through an anterior or posterior approach. For proper balance it should be used in pairs. Outcomes of a cadaveric study of the biomechanics of this implant were favorable. The cadaveric model, however, failed to permit full hydration of the device. Since 1996, 423 patients have received the PDN with a surgical success rate of 90% and clinical results have been encouraging. The main problem of a 10% implant migration rate, has led to a series of modifications to the procedure for installation.

Another example of a nucleus replacement includes the AQUARELLE STRYKER (available from Howmedica of Rutherford, N.J.) (not shown) which is a hydrogel material based on polyvinyl alcohol that is hydrated before implantation. This material can be implanted through a tapered cannula placed in an annulotomy via a posterior or lateral approach. Finally, the PROSTHETIC INTERVERTEBRAL NUCLEUS (available from Raymedica of Bloomington, Minn.) (not shown) is another example of a nucleus replacement. It is a polyurethane material instilled into a balloon that is inserted into a disc space. Once placed into the disc space, the chamber is filled with the material, which then cures in situ.

In contrast to nucleus replacement, total disc replacement addresses degenerative processes throughout the intervertebral disc. It represents a surgical procedure similar to that required with anterior cervical discectomies and corpectomies. These prosthetics are designed to restore the normal movement of the diseased motion segment. Using technology gained from orthopedic joint replacements, numerous strategies have been devised to create a successful prosthetic disc. Generally, prosthetic discs comprise a polymer center bounded by metallic end-plates with prongs or spikes to abut against the surrounding bone segments to prevent motion. Elastomers, viscous fluids, fluid-filled chambers, and articulating components have been used in prosthetic discs. Strength, durability, biomechanical and biochemical compatibility, ease of implantation, and the immediate postoperative and long-term stability of the device must be considered and will affect the utility of a replacement disc.

In the lumbar spine, the LINK SB CHARITÉ III (available from Waldemar Link GmbH and Co. of Hamburg, Germany), PRODISC (available from Aesculap AG and Co. of Tuttlingen, Germany), and ACROFLEX-100 prosthesis (available from DePuy AcroMed of Raynham, Mass.) are the most widely implanted total-disc replacements (see FIGS. 2B-2D, respectively).

In 1984, Drs. Karin Büttner-Janz and Kurt Schellnack began to work with the Waldemar Link GmbH & Company (Hamburg, Germany) to develop a replacement lumbar disc. After several design iterations, the final version of the disc, the LINK SB CHARITÉ III (generally designated LSBC in FIG. 2B) is currently available in Europe. The device is composed of an ultrahigh molecular weight core C sandwiched between two cobalt-chromium alloy endplates EP. More than 3000 of these discs (all generations) have been implanted throughout Europe. In 1994, a multicenter retrospective review of the early clinical results with the LINK SB CHARITÉ III lumbar artificial disc was published. Pain reduction, mobility, walking distance, and strength improved significantly in 93 patients when compared to their preoperative condition. The complication rate, as a result of disc migration or dislocation and device failure, was 6.5%. In another study by others of the LINK SB CHARITÉ III disc, forty-six patients were studied a mean of 3.2 years after implantation: 63% reported satisfactory results. The success rate was 69% in patients who underwent isolated disc replacement and 77% in patients who had undergone previous back surgery. Two patients had the prosthesis removed. Seven patients underwent posterolateral fusion without removal of the device.

The PRODISC (generally designated PD in FIG. 2C), developed by Dr. Thierry Marnay, consists of two CrCoMo alloy endplates EP covered with titanium plasmopore to enhance osteointegration (FIG. 2C shows one endplate of the PRODISC artificial disc). The inferior articulation is a mono-convex surface that slides into a concave upper rim. This design permits the implant to be inserted with significantly less distraction of the disc space than the LINK SB CHARITÉ III disc. Because movement is across two surfaces, the motion is semiconstrained. The clinical outcomes associated with the PRODISC have been presented at several meetings, but published data are limited.

Another study has reported experience with the ACROF-LEX-100 artificial lumbar disc (generally designated AF in FIG. 2D). This prosthesis consists of two titanium endplates EP vulcanized to a polyolefin rubber core C. The disc was implanted in six patients via a midline transabdominal approach, four of whom reported satisfactory results. In one patient, the rubber core fractured and a revision was necessary.

In the cervical spine, the CUMMINS/BRISTOL disc (available from Medtronic Sofamor Danek of Memphis, Tenn.) (not shown) and the BRYAN CERVICAL DISC prosthesis (available from Medtronic Sofamor Danek of Memphis, Tenn.) (generally designated BCD in FIG. 2E) are under investigation. The CUMMINS/BRISTOL disc consists entirely of stainless steel or titanium and is of ball and socket construct. Because it is screwed into place, this artificial disc can only be used for single-level disc disease. The BRYAN CERVICAL DISC BCD is a composite-type disc prosthetic designed with a wear resistant, low friction, elastic nucleus C and two anatomically shaped metal plates EP on either side of the nucleus. In Europe, the BRYAN CERVICAL DISC prosthesis has been implanted in 97 patients, and has had favorable results for the purpose of disc replacement only.

These discs represent the first generation of spinal arthroplasty devices and a number of concerns have arisen from the possible use of these artificial discs. One disadvantage of prior art prosthetic discs involves the interface that exists between the prosthetic and the adjacent vertebrae structure. Wear or "micro-motion" can cause debris to accumulate either within the prosthetic disc or the artificial joint space. Additionally, one of the greatest concerns of prosthetic disc replacement is that of implant migration. While more leeway for implant migration exists in the lumbar spine, disc migration can have grave consequences in the cervical spine. Artificial disc migration can result in devastating neurological injury, so disc migration prevention is paramount in importance.

While disc arthroplasty using artificial discs may help solve the biomechanical problems associated with spine fusion, this technology primarily benefits patients who have disc disease. Even if artificial discs are approved in the US, they would not help those patients with non-disc related forms of spinal disease, such as spinal fracture or scoliosis, that currently require spinal fusion. Also, there exist numerous disadvantages of using artificial discs exclusively as discussed hereinabove. Therefore, there remains a long-felt need for a spine replacement system that can address all forms of subaxial spine and disc disease, that recreates the anterior and middle columns of the subaxial spine complete with adjacent motion segments, and that does not possess the disadvantages of prior art prosthetics.

SUMMARY

Apparatuses and methods for recreating the anterior and middle columns of the subaxial spine complete with adjacent motion segments are provided in accordance with the subject matter disclosed herein.

According to one aspect, a surgical implant assembly for replacement of a spine segment is provided comprising a first cage adapted to be rigidly attached to a first vertebra and a second cage adapted to be rigidly attached to a second vertebra. The surgical implant assembly further comprises a spinal disc replacement prosthesis having an upper surface and a lower surface wherein the disc replacement prosthesis is positioned between the first and second cages.

According to another aspect, a method for replacement of a spine segment with a surgical implant assembly is provided comprising the steps of providing a surgical implant assembly comprising a first cage adapted to be rigidly attached to a first vertebra, a second cage adapted to be rigidly attached to a second vertebra, and a spinal disc replacement prosthesis having an upper surface and a lower surface wherein the disc replacement prosthesis is positioned between the first and second cages and wherein the disc replacement prosthesis comprises at least one fluid-filled compartment. The method further comprises removing a spinal disc positioned between an upper vertebra and a lower vertebra, removing the bottom portion of the upper vertebra, removing the upper portion of the lower vertebra, inserting the surgical implant assembly between the upper and lower vertebrae, and affixing the surgical implant assembly at each end thereof to the upper and lower vertebrae, respectively.

According to a further aspect, an artificial spinal disc replacement prosthesis is provided comprising a resilient body of silicone, plastic elastomer, or other similar material having two or more fluid-filled compartments that are each adjustably fluid filled by a respective port defined in the prosthesis body.

It is therefore an object of the present subject matter to provide a spine replacement system that avoids prosthetic movement or migration.

It is another object of the present subject matter to provide a spine replacement system that includes an adjustable prosthetic disc element to modulate kyphosis, lordosis, and scoliosis.

It is yet a further object of the present subject matter to provide a spine replacement system that represents segmental spine portions, as well as disc replacement, for the treatment of traumatic spinal instability, congenital spinal deformity, and severe spondylosis in addition to degenerative disc disease.

Some of the objects of the present subject matter having been stated hereinabove, and which are addressed in whole or in part by the present subject matter, other objects will become evident as the description proceeds when taken in connection with the accompanying drawings as best described hereinbelow.

DETAILED DESCRIPTION

The subject matter disclosed herein relates to apparatuses and methods for recreating the anterior and middle columns of the subaxial spine complete with adjacent motion segments. These apparatuses may be used to replace both a single damaged disc and portions of the adjacent vertebrae as well as entire segments of the spine for the repair of spinal discs or vertebrae damaged by injury or disease. It can be appreciated that while the subject matter disclosed herein refers to a human spinal column, the subject matter disclosed herein may also be applicable to any vertebral animal.

DEFINITIONS

The following definitions are used throughout this description. The terms "anterior" and "posterior" mean toward the front or toward the back of the body, respectively. For example, a discussion of the anterior portion of the vertebral body refers to the portion of the vertebra that is toward the front of the body. The terms "superior" and "inferior" mean upper and lower, respectively. For example, in a discussion of two adjacent vertebrae, the superior vertebra refers to the vertebra that is located above the inferior vertebra. Also, the inferior portion of a superior vertebra would be the lower portion of the upper vertebra. The terms "medial" and "lateral" mean nearer the median plain or further from the median plane, respectively. The median plain is an imaginary vertical plane through the middle of the body that divides the body into right and left halves.

As described above, the spine is made up of 24 vertebrae and is typically described and defined by physicians in terms of levels that center at the vertebral bodies of each of the 7 cervical, 12 thoracic, and 5 lumbar spinal segments. By this "vertebrae-centric" nomenclature, each adjacent spinal disc is an intervertebral disc.

A "disc-centric" model of the spine would instead number discs consecutively and each vertebra would be conceptually defined as an interdiscal vertebra. Each segmental unit of the spine, in a disc-centric model, would be composed of the spinal disc, the inferior half of the vertebral body above, and the superior half of the vertebral body below. The subject matter disclosed herein is based upon a disc-centric model of the spine.

Elements of Surgical Implant Assembly

Figure 1A:
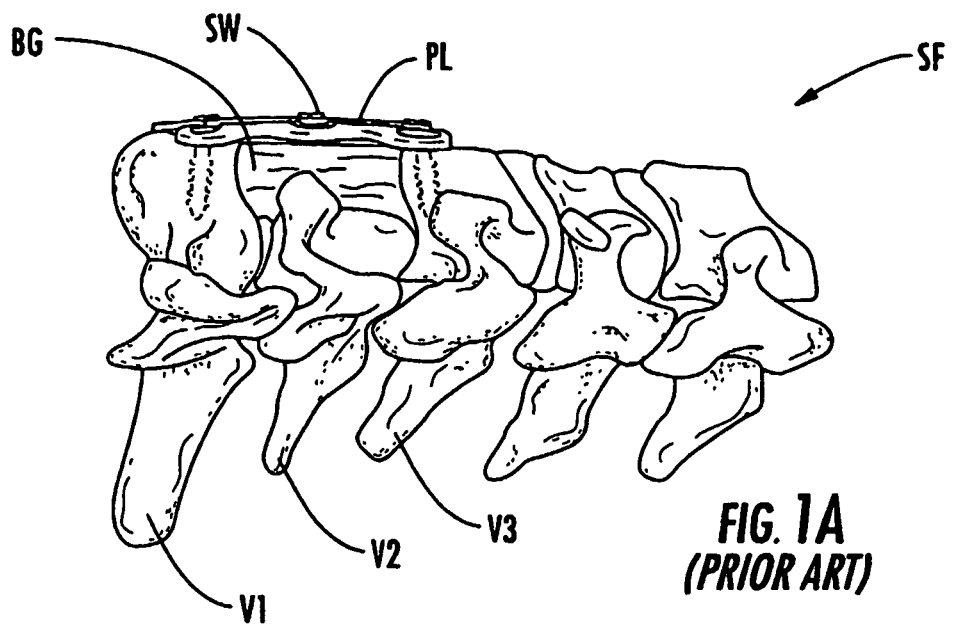
FIGS. 1A and 1B are side and plan views of arthrodesis (spine fusion) in accordance with the prior art.
Figure 1B:
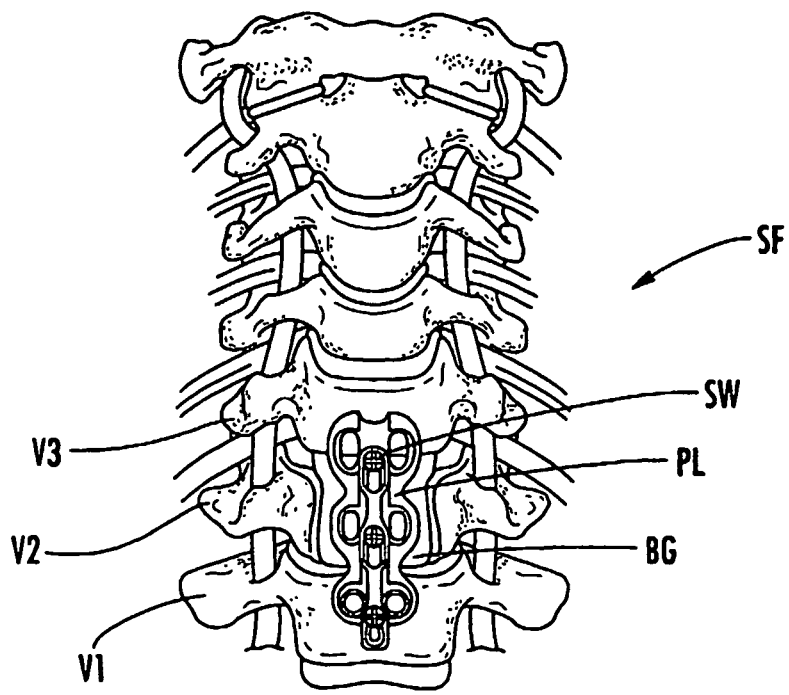
Figure 2A:
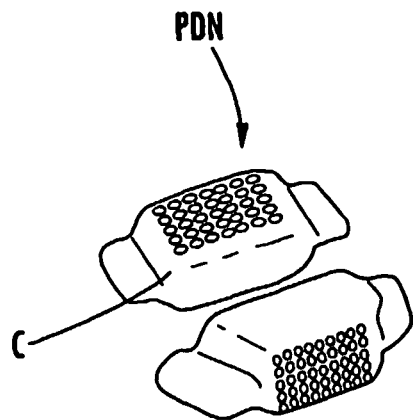
FIGS. 2A-2E are perspective views of nucleus replacements and artificial discs in accordance with the prior art.
Figure 2B:
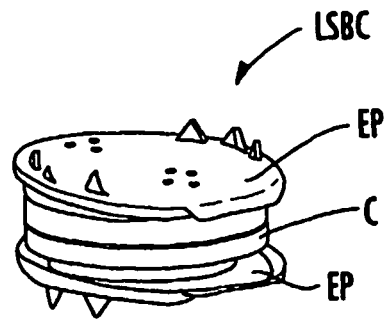
Figure 2C:
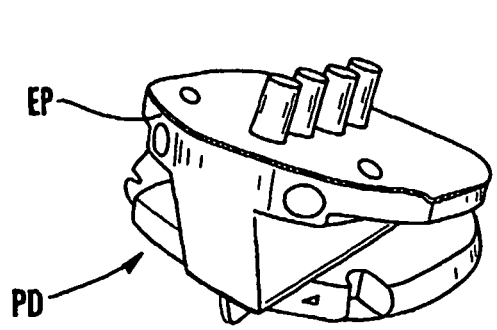
Figure 2D:
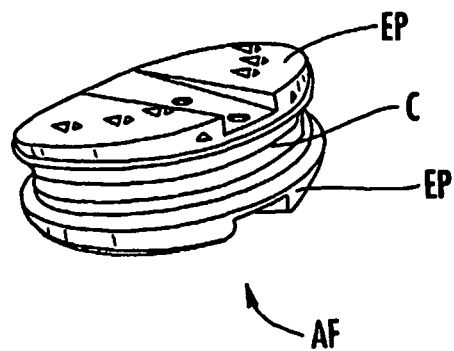
Figure 2E:
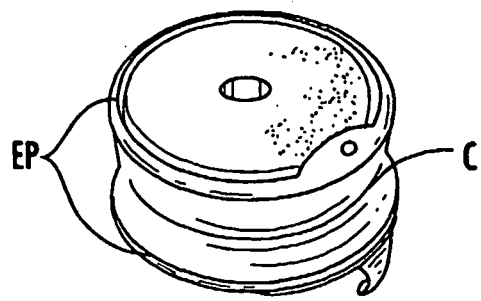
Figure 3:
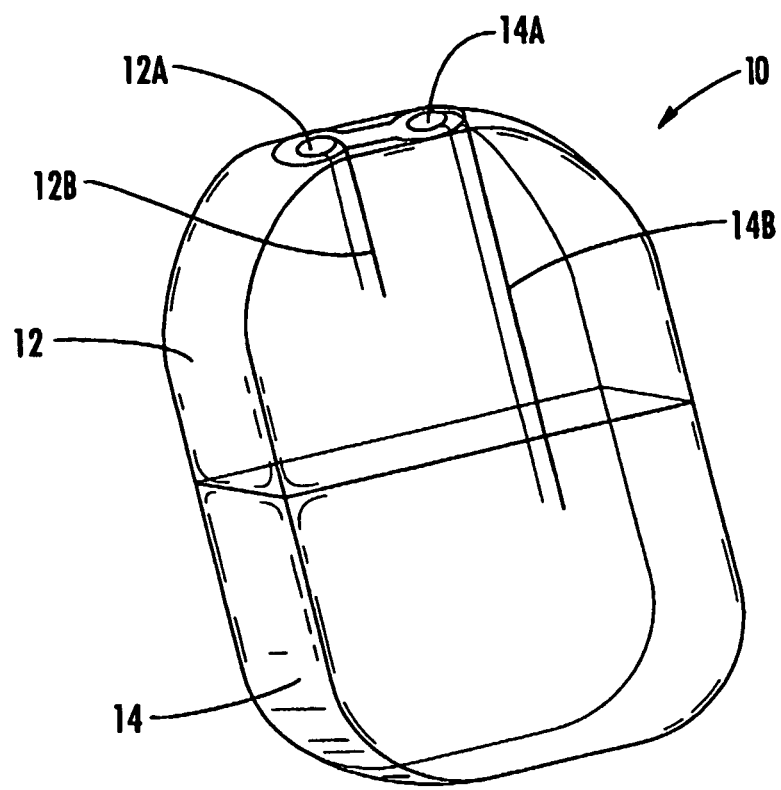
FIG. 3 is a perspective view of a prosthetic disc provided in accordance with one embodiment of the present subject matter.
Figure 4:
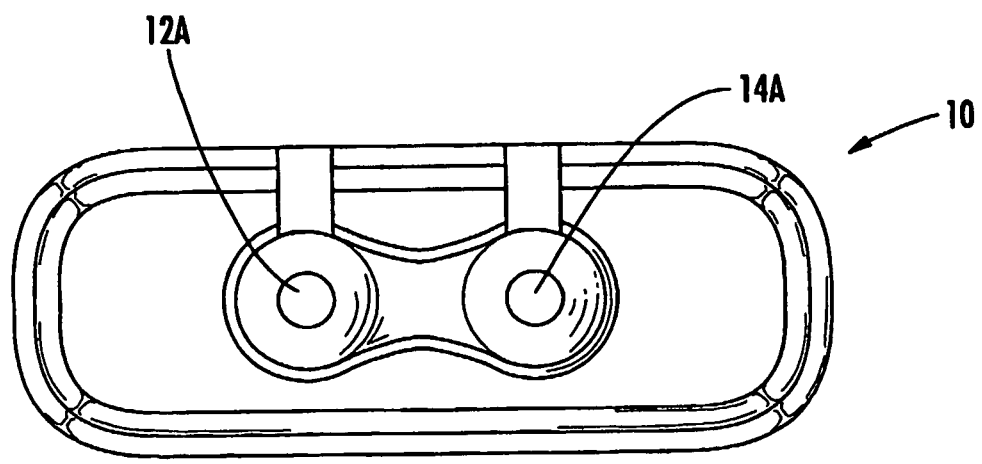
FIG. 4 is a top plan view of a prosthetic disc provided in accordance with one embodiment of the present subject matter.

Referring now to FIGS. 3 and 4, one element of the surgical implant assembly of the present subject matter comprises a spinal disc replacement prosthesis 10. Prosthetic disc 10 comprises a flexible or an expandable structure having an exterior surface and a hollow interior. The flexibility of the construct allows the structure to be capable of being compressed such that the construct occupies less than the maximum amount of volume theoretically possible for the construct. The expandability of the construct allows the structure to be increased significantly by increasing the internal pressure of the construct, such as by filling the internal areas with a desired fluid. Disc 10 may be constructed of a biocompatible material having suitable strength and resistance to tearing to accept the dynamic loading required of a spinal disc. Such material may include polymer material such as polyethylene, polyamide, polypropylene, polyester, polycarbonate, polysulfone, or alternatively fibrous hydrogel or glass. Any other material known to those of skill in the art may be used to construct disc 10.

Disc 10 may be compartmentalized into a fluid-fillable anterior compartment 12 and a fluid-fillable posterior compartment 14 for the alteration of the degree of movement at the motion segment and to alter the degree of flexion or extension available to this segment, as will be described in more detail hereinbelow. As an alternative, such as for the treatment of scoliosis (abnormal side-to-side or lateral curves in the spinal column), disc 10 may be compartmentalized into left and right compartments (not shown) for the adjustment of the motion segment for lateral flexion.

Anterior compartment 12 of disc 10 is accessed directly or percutaneously via anterior infusion port 12A and anterior infusion tube 12B for expansion (fluid filling) or contraction (fluid removal). Posterior compartment 14 is accessed directly or percutaneously via posterior infusion port 14A and posterior infusion tube 14B for expansion or contraction. Anterior infusion port 12A and posterior infusion port 14A are disposed through the wall of disc 10 and comprise a bore of any desired shape, wherein the bore is in communication between the exterior surface of disc 10 and the interior of disc 10, via anterior infusion tube 12B and posterior infusion tube 14B. Fluid may be placed into anterior infusion port 12A or posterior infusion port 14A by any method known to those of skill in the art, such as by injection or pumping, until anterior compartment 12 or posterior compartment 14 are filled to the desired shape and size. Anterior infusion port 12A and posterior infusion port 14A may comprise a valve for control of fluid into and out of disc 10. It will be appreciated that the greater amount of fluid within anterior compartment 12 and posterior compartment 14 will decrease the degree of movement available within the motion segment and vice-versa.

In their inflated state, anterior compartment 12 and posterior compartment 14 are filled with a viscous biocompatible fluid (not shown) having the mechanical properties of a natural spinal disc nucleus. For example, fluids may comprise polyethylene, polyamide, polypropylene, polyester, polycarbonate, polysulfone, hydrogel, a silicone-gel and silicone rubber.

Figure 5:
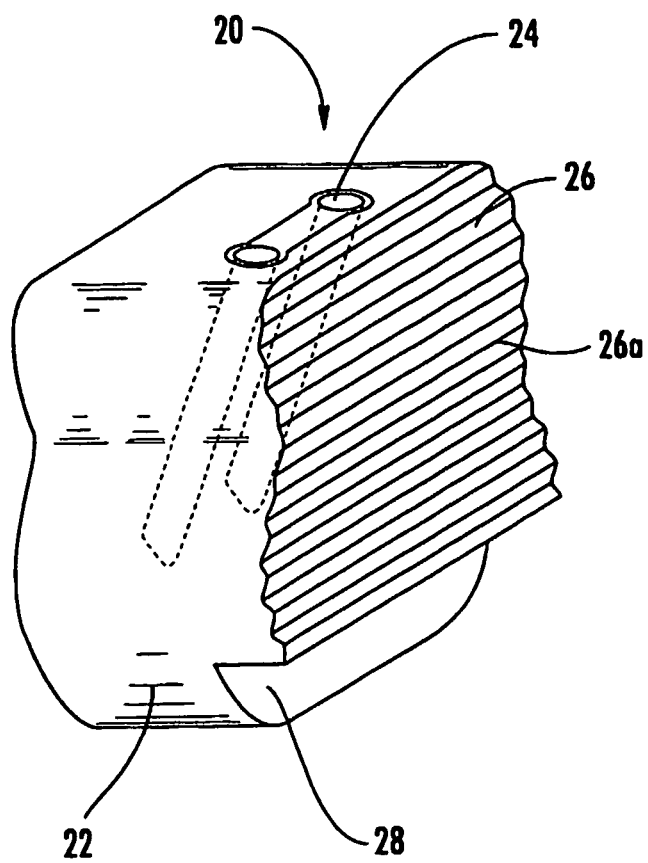
FIG. 5 is a perspective view of a cage element provided in accordance with one embodiment of the present subject matter.
Figure 6:
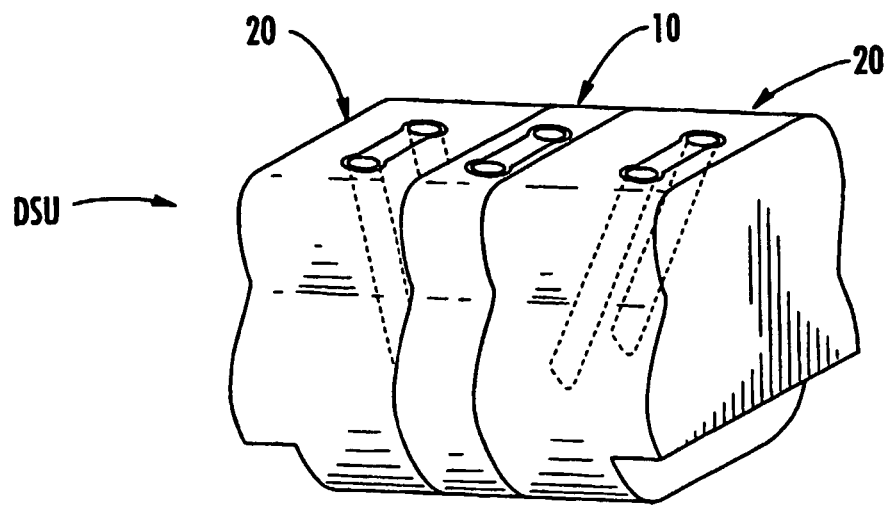
FIG. 6 is a perspective view of a disc-centric segmental unit (DSU) provided in accordance with one embodiment of the present subject matter.

Referring now to FIG. 5, another element of the surgical implant of the present subject matter includes a spinal fusion cage element 20 designed for joining with prosthetic disc 10 and an adjacent vertebral body. As will be described in more detail hereinbelow and as shown in FIG. 6, a surgical implant assembly or disc-centric segmental unit DSU can be created by the joining, in a sandwich or laminate configuration, two cage elements 20 and a prosthetic disc 10. Cage elements 20 can be affixed to spinal prosthetic disc 10 by an adhesive or other cementious material.

Referring back to FIG. 5, cage element 20 comprises a cage body 22 constructed of any material known to those of skill in the art for construction of bone cages. Cage body 22 is preferably constructed of carbon fiber that better approximates the elastic modulus of bone material, but may be constructed of of other materials including ceramics, metals, polymers, or other synthetics. Preferably, the construction of cage body 22 is designed to fuse cage element 20 with a remaining segmented hemi-vertebral body resulting from the surgeon performing hemicorpectomies on the bottom half of an upper vertebra and the top half of a lower vertebra in preparation for installation of disc-centric segmental unit DSU, as will described in further detail hereinbelow. This preferable construction of cage body 22 includes a three-dimensional weaving of carbon fibers resulting in a mesh that provides interstices for the in-growth of bone mass when joined with the hemi-vertebral body so that cage element 20 and the adjacent vertebral body become one biomechanically. Bone fusion is a concept known to those of skill in the art, such as exhibited by the many different bone fusion cages currently in use as spinal grafts, and therefore this concept will not be discussed in any further detail.

Cage element 20 may further comprise one or more channels 24 through which bone screws S or other fasteners can be used in conjunction with a mounting plate P system (see FIGS. 8-10) to secure cage element 20 to the remaining hemi-vertebral body, or to each other in the case of multiple disc-centric segmental unit DSU construction. This fastening procedure will be discussed in more detail hereinbelow.

The outside surface 26 of cage element 20 that is remote from prosthetic disc 10 when joined together may further comprise ridges 26A. Surface 26 is the interface between cage element 20 and the hemi-vertebral body or, in the case of multiple disc-centric segmental unit DSU construction, surface 26 is the interface between cage element 20 and another cage element 20. When cage element 20 is being interfaced with a hemi-vertebral body, ridges 26A provide a higher friction surface for the interface joint to further prevent slippage when used in conjunction with mounting plates P and bone screws S (see FIGS. 8-10). When cage element 20 is being interfaced with another cage element 20 for creation of a multiple disc-centric segmental unit DSU or "stack" of DSUs (described hereinbelow), ridges 26A on each of cage elements 20 will matingly engage one another to form a non-slip fit prior to securing by screws and mounting plates.

In order to further prevent posterior migration of cage element 20 toward the spinal cord when attached to a hemi-vertebral body, cage element 20 may further comprise a notch or groove 28 constructed in the posterior end of cage body 22 as shown in FIG. 5. As will be described in further detail hereinbelow, when performing a hemi-corpectomy to remove half of the adjacent vertebral body, the surgeon will leave a portion of the vertebral body next to the posterior portion of the vertebra in order to create a bone shoulder. When cage element 20 is attached to the adjacent vertebra, groove 28 of cage element 20 matingly engages the bone shoulder of the vertebra. This engagement, in conjunction with attachment provided by a mounting plate P and screws S (see FIGS. 8-10), leads to cage element 20 (and attached prosthetic disc 10 in the case of multiple disc-centric segmental unit DSU construction) being non-migratable. This benefit of preventing migration of the surgical implant is of utmost importance in spinal disc or vertebra repair.

Pre-Installation Assembly of Surgical Implant Assembly

Figure 7:
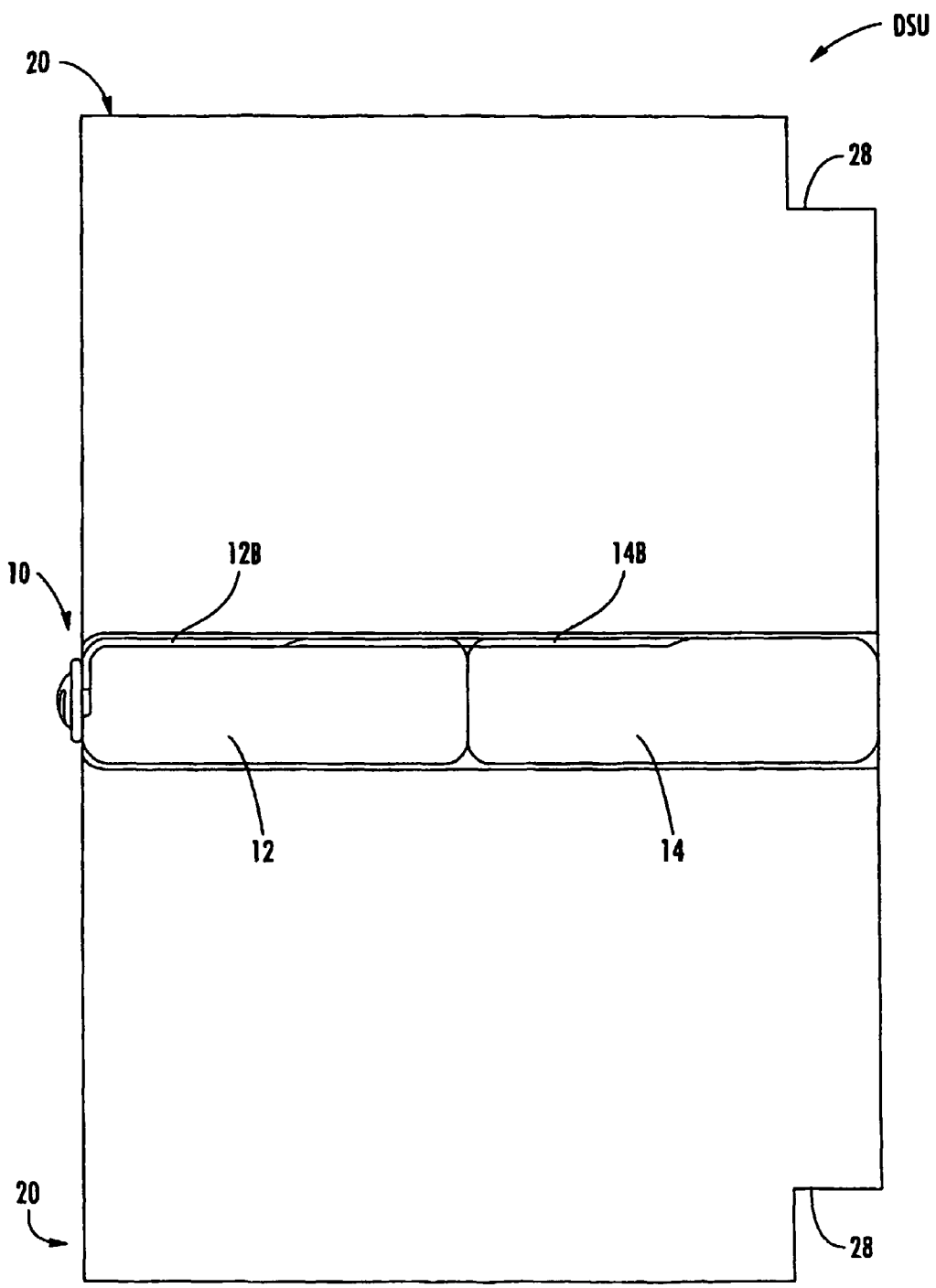
FIG. 7 is a side elevation view of a disc-centric segmental unit (DSU) provided in accordance with one embodiment of the present subject matter.

Referring now to FIGS. 6 and 7 and as discussed briefly hereinabove, a surgical implant assembly or disc-centric segmental unit DSU may be constructed as an individual unit comprising the joining of two cage elements 20 and a prosthetic disc 10. In this combination, prosthetic disc 10 will be placed as the middle element and will be manufactured as one unit with the two other elements: two cage elements 20 being placed superiorly and inferiorly, with each cage element 20 intended to replace half of an adjacent spinal vertebral body. These three elements as a single disc-centric segmental unit DSU replace the anterior elements of one disc-centric segment of the vertebral spine. The combining of the two cage elements 20 and prosthetic disc 10 can be accomplished through any method known to those of skill in the art, such as gluing, cementing, vulcanization, etc. For example, manufacturing methods such as those used to combine metal end plates with elastomeric discs in prior art artificial discs may be used.

Disc-centric segmental unit DSU is the building block within the framework of a segmental spinal replacement system and can be used to recreate the anterior and middle columns of the subaxial spine complete with adjacent motion segments. If only one disc-centric segmental unit DSU is used to replace a damaged spinal disc and a portion of adjacent vertebrae, the procedure for installation of the unit would be termed Disc-centric Segmental Arthroplasty (DSA). This "segmental" spinal replacement would replace both bone and disc elements of an entire segmental unit in the anterior two columns of the spine. However, it is envisioned by the design of disc-centric segmental unit DSU that these units are stackable and therefore two or more disc-centric segmental units DSU could be stacked and combined to recreate a portion of the segmented spine anteriorly. This linking and stacking of multiple disc-centric segmental units DSU would permit the spine surgeon to recreate an artificial subaxial spine of whatever length necessary, complete with all adjacent motion segments. For example, two stacked disc-centric segmental units DSU form a prosthesis that can replace a vertebral body and its adjacent motion segments. Analogously, three disc-centric segmental units DSU replace two vertebral bodies and their adjacent motion segments. In such fashion, multiple stacked DSUs recreate vertebral body segments of the subaxial spine, and thus comprise a disc-centric spinal replacement DSR system. In the DSR system of stacked disc-centric segmental units DSU, opposing cage elements are mechanically joined and need not necessarily be porous, while the cages at each end of the prosthesis must be porous for bone in-growth with the adjacent vertebrae.

Each motion segment of disc-centric segmental unit DSU is capable of being individually adjusted by fluid infusion adjustment of built-in anterior compartment 12 and posterior compartment 14 of prosthetic disc 10, as discussed hereinabove, in order to achieve the ideal spinal curvature and range of motion for physiologically correct form and function.

Installation of Surgical Implant Assembly

Figure 8:
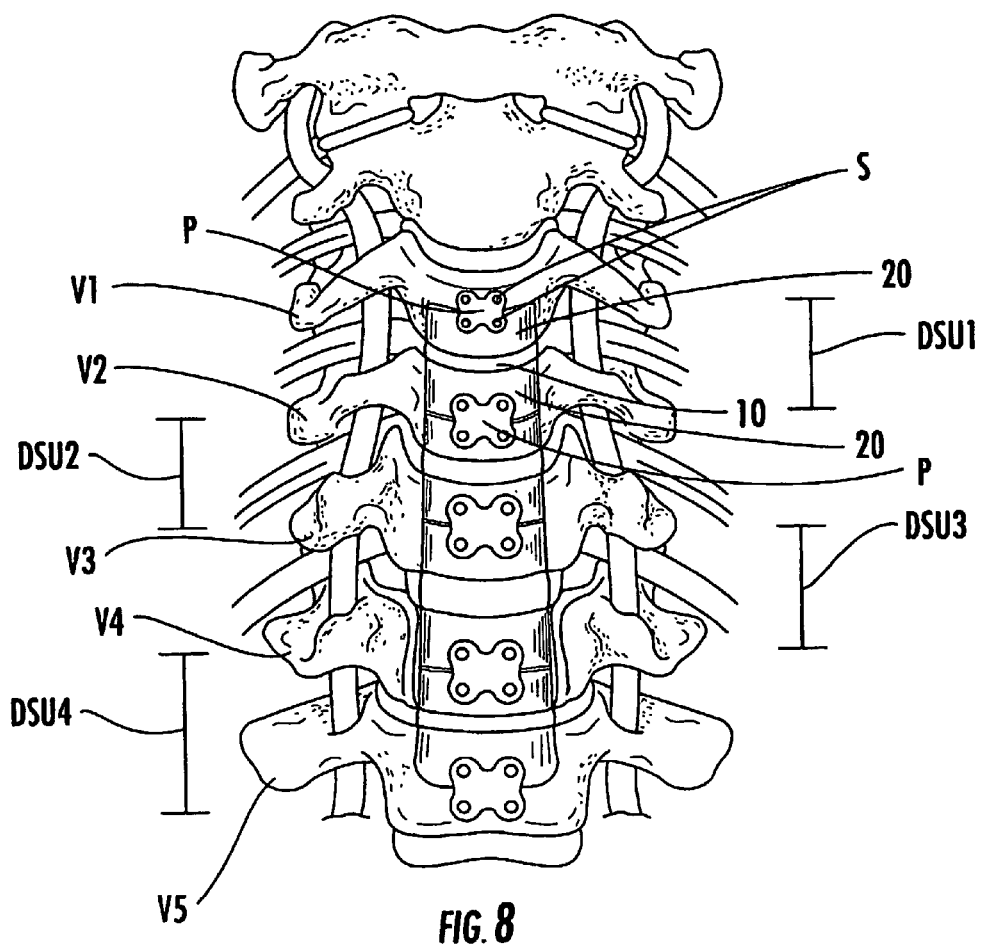
FIG. 8 is an anterior cut-away plan view of a plurality or stack of disc-centric segmental units (DSUs) inserted into a spine in accordance with one embodiment of the present subject matter.
Figure 9:
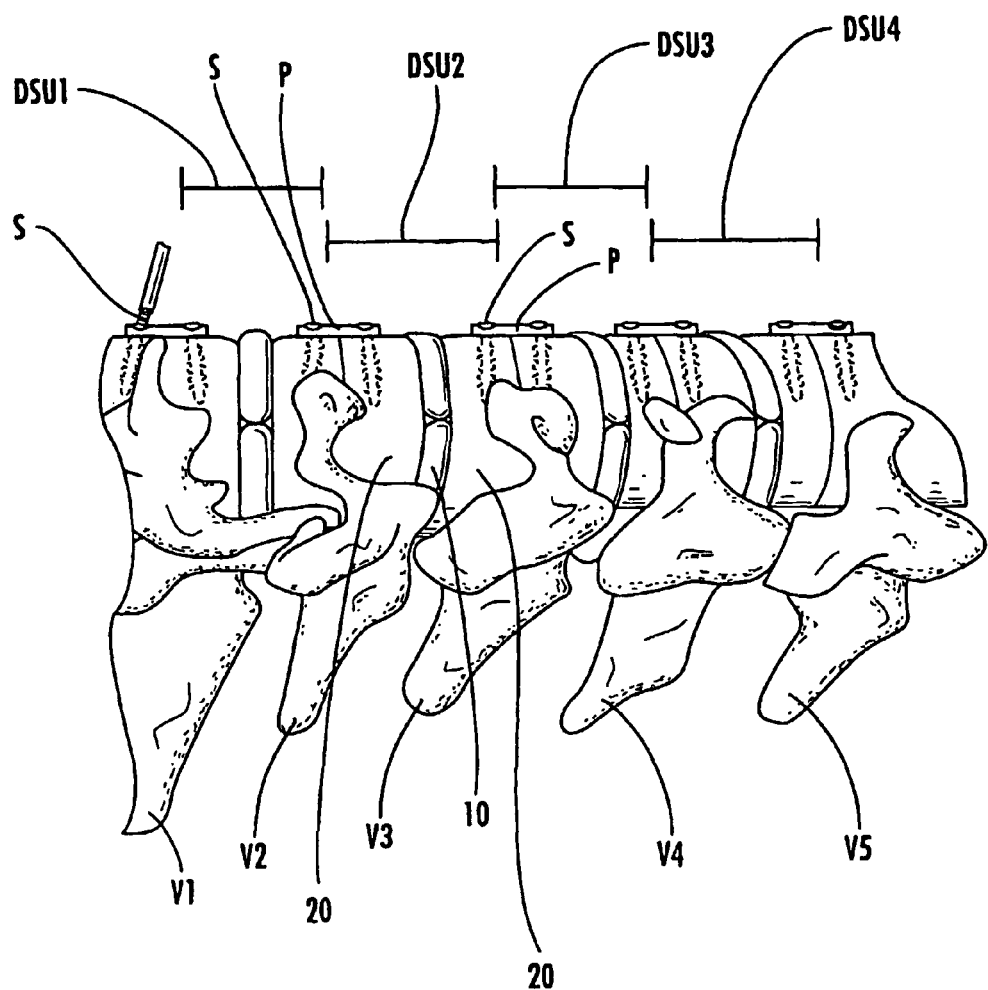
FIG. 9 is a lateral cut-away side view of a plurality or stack of disc-centric segmental units (DSUs) inserted into a spine in accordance with one embodiment of the present subject matter.

The installation of a single disc-centric segmental unit DSU for replacement of a diseased or damaged disc will now be described. FIGS. 8 and 9 show anterior and lateral cutaway views, respectively, of four (4) disc-centric segmental units DSU1-DSU4 installed between vertebral bodies V1V5, respectively. These replacements would represent indications that usually require multiple level anterior cervical discectomy with plating (fusion). However, the method described below will describe the placement of a single disc-centric segmental unit DSU1 between two vertebral bodies V1, V2. The installation of a stack of multiple disc-centric segmental units DSU will be described thereafter.

The first step in installation of single disc-centric segmental unit DSU1 would be gaining access to the region of interest and the removal of the diseased or damaged disc, such as that between vertebrae V1, V2, by methods known to those of skill in the art. In addition to discectomy, the surgeon would perform hemicorpectomies on the bottom half of vertebra V1 and the top half of vertebra V2. Where significant height loss already exists in a degenerate spine, bony removal less extensive than a hemicorpectomy may be performed so that the end goal would also be to restore vertebral body height. As described hereinabove in relation to groove 28 of cage element 20, when performing the hemicorpectomy on each adjacent vertebral body, the surgeon will leave a portion of the body next to the posterior portion of the vertebrae in order to create a bone shoulder (not shown) for mating engagement with groove 28 of cage element 20 to prevent posterior migration.

Once natural disc removal and bone preparation is complete, the region is set for implant installation. Disc-centric segmental unit DSU1, a biomechanical equivalent of the segment resected, is then placed into the surgical resection bed between vertebral bodies V1, V2 using appropriate instruments. With this placement, the ridged outside surface 26 of each of cage elements 20 is placed against the corresponding adjacent vertebral bodies V1, V2 for vertical placement and prevention of vertical migration. Groove 28 of each of cage elements 20 is placed against the corresponding bone shoulder (not shown) of adjacent vertebral bodies V1, V2 for lateral placement and prevention of posterior migration. Anterior migration of disc-centric segmental unit DSU1 will be prevented by the placement of screw plate P, described hereinbelow.

Disc-centric segmental unit DSU1 is then temporarily secured in place for migration prevention prior to full bone fusion. The surgeon will place screw plates P over each of cage elements 20 of disc-centric segmental unit DSU1 and the adjacent hemivertebrae V1, V2. Screws S or other appropriate fasteners are then placed through the portion of plate P over cage elements 20 and are screwed into channels 24. Bone screws S or other appropriate fasteners known to those of skill in the art are then placed through the portion of plate P over adjacent hemivertebrae V1, V2 and are screwed into a secured position.

With the securing of plates P onto disc-centric segmental unit DSU1 and adjacent hemivertebrae V1, V2, disc-centric segmental unit DSU1 is prevented from migration in any direction. As described hereinabove, ridged outside surface 26 of each of cage elements 20 is placed against the corresponding adjacent vertebral bodies V1, V2 and prevents vertical migration; groove 28 of each of cage elements 20 is placed against the corresponding bone shoulder of adjacent vertebral bodies V1, V2 and prevents posterior migration; and placement of plates P against disc-centric segmental unit DSU1 and adjacent vertebral bodies V1, V2 prevents anterior migration.

Once disc-centric segmental unit DSU1 is firmly placed and secured, each of cage elements 20 is filled with fusion seed material, such as bone graft, bone substitutes with aspirated bone marrow, or bone morphogenetic protein (BMP) preparations such as rhBMP-2 Infuse Bone Graft, in order to promote bony fusion. With time, a solid fusion is expected between each cage element 20 on either side of prosthetic disc 10 and the remaining adjacent hemivertebrae V1, V2.

Prior to closing, the surgeon will expand prosthetic disc 10 to the proper size and shape. As discussed hereinabove, anterior compartment 12 and posterior compartment 14 of prosthetic disc 10 can be expanded to desired shape by the filling or removal of fluid via anterior infusion port 12A and anterior infusion tube 12B, and posterior infusion port 14A and posterior infusion tube 14B, respectively. The surgeon may place fluid into anterior infusion port 12A or posterior infusion port 14A by any method known to those of skill in the art, such as by injection or pumping, until anterior compartment 12 or posterior compartment 14 are filled to the desired shape and size. The adjustability of prosthetic disc element 10 allows the surgeon to modulate kyphosis and lordosis, or even scoliosis (in the case of left and right compartments).

The surgeon then closes the incision and the procedure is complete.

Figure 10:
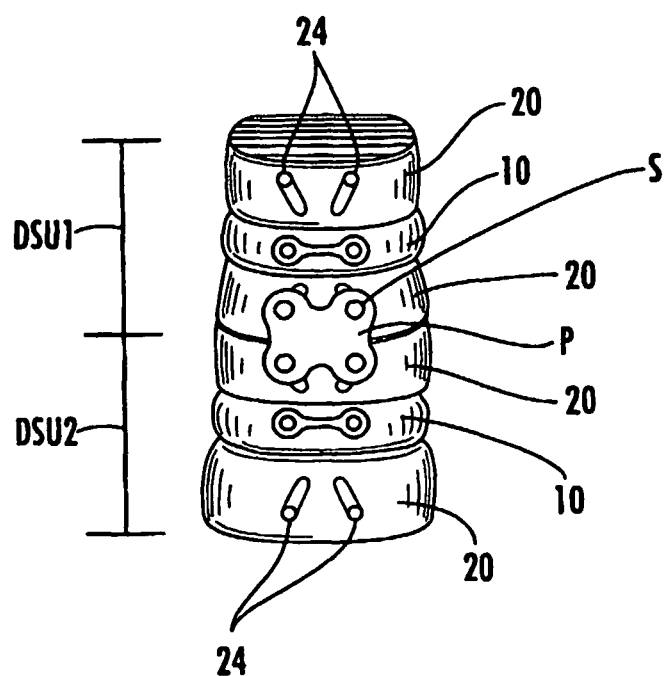
FIG. 10 is a front perspective view of two (2) disc-centric segmental units (DSUs) stacked together in accordance with one embodiment of the present subject matter.

As discussed hereinabove and with reference to FIGS. 8-10, spine disease spanning multiple segments may be addressed by the present subject matter through the use of individual disc-centric segmental units, such as DSU1-DSU4, being linked and stacked into long constructs with adjacent motion segments capable of physiologic flexion and extension. In such a case, the surgeon would repeat the procedures as described hereinabove, except the adjacent inboard cage elements 20 of the individual disc-centric segmental units DSU1-DSU4 would be fixedly secured to each other in some mechanical fashion, such as via plates P and screws S. Outboard cage elements at the superior and inferior ends of the prosthesis 20 would be secured to adjacent hemivertebrae V1 and V5 as described hereinabove.

This linking of individual disc-centric segmental units DSU1 DSU4 would allow the spine surgeon to artificially recreate the anterior and middle columns of the subaxial spine, complete with all adjacent motion segments. Each motion segment (prosthetic disc 10) could be individually adjusted by infusion adjustment of the built-in anterior and posterior disc chambers to achieve the ideal spinal curvature and range of motion for physiologically correct form and function.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A surgical implant assembly for replacement of a spine segment comprising:
   at least two disc-centric segmental units, each disc-centric segmental unit comprising:
      (a) a first spinal fusion cage configured to replace a portion of a first spinal vertebral body and adapted to be rigidly attached to a remaining portion of the first spinal vertebral body;
      (b) a second spinal fusion cage configured to replace a portion of a second spinal vertebral body and adapted to be rigidly attached to a remaining portion of the second spinal vertebral body; and
      (c) a spinal disc replacement prosthesis having an upper surface and a lower surface wherein the disc replacement prosthesis is positioned between the first and second cages, the spinal disc replacement prosthesis comprising a resilient plastic or elastomeric body having an anterior compartment for receiving fluid and a posterior compartment for receiving fluid; and
   the disc-centric segmental units being stackable to replace a damaged portion of a spine;
   wherein the first spinal fusion cage is configured to replace about half of the first spinal vertebral body and the second spinal fusion cage is configured to replace about half of the second spinal vertebral body.

2. The surgical implant assembly of claim 1 wherein the first and second cages are constructed of material selected from the group consisting of carbon fiber, ceramics, metals, polymers and synthetics.

3. The surgical implant assembly of claim 2 wherein the first and second cages are constructed of carbon fiber.

4. The surgical implant assembly of claim 3 wherein the first and second cages are constructed of a carbon fiber mesh throughout that forms interstices within the first and second cages.

5. The surgical implant assembly of claim 2 wherein the first and second cages each define at least one channel therein for receiving a screw.

6. The surgical implant assembly of claim 2 wherein the first and second cages each define an inner surface adjacent the spinal disc replacement prosthesis and an outer surface, and wherein the outer surfaces each define ridges thereon.

7. The surgical implant assembly of claim 6 wherein the first and second cages each define a groove in a portion of the circumference of the outer surface thereof to prevent posterior migration of the surgical implant assembly.

8. The surgical implant assembly of claim 1 wherein at least one of the compartments for receiving fluid is filled with a silicone-gel fluid.

9. The surgical implant assembly of claim 1 wherein at least one of the compartments for receiving fluid is adjustably filled with the fluid.

10. The surgical implant assembly of claim 1 wherein the two adjustably compartments for receiving fluid each has a port within the spinal disc replacement prosthesis through which each compartment receives fluid.

11. The surgical implant assembly of claim 1 wherein the first and second cages are affixed to the spinal disc replacement prosthesis by an adhesive.

12. The surgical implant assembly of claim 1 wherein the surgical implant assembly is securable to the first and second spinal vertebral bodies at each respective end of the surgical implant assembly by a screw plate.

13. The surgical implant assembly of claim 1 comprising two or more of the disc-centric segmental units secured together in a stack to replace a damaged portion of a spine.

14. The surgical implant assembly of claim 1 wherein the first and second spinal vertebral bodies are selected from the group consisting of cervical, thoracic, and lumbar vertebrae.

15. A surgical implant assembly for replacement of a spine segment comprising:
   at least two disc-centric segmental units, each disc-centric segmental unit comprising:
      (a) a first carbon fiber spinal fusion cage configured to replace a portion of a first spinal vertebral body and adapted to be rigidly attached to a remaining portion of the first spinal vertebral body;
      (b) a second carbon fiber spinal fusion cage configured to replace a portion of a second spinal vertebral body and adapted to be rigidly attached to a remaining portion of the second spinal vertebral body; and (c) a spinal disc replacement prosthesis having a resilient plastic or elastomeric body defining an upper surface and a lower surface wherein the disc replacement prosthesis is positioned between the first and second cages and wherein the disc replacement prosthesis comprises two adjustably compartments for receiving fluid with one compartment in an anterior position and one compartment in a posterior position; and the disc-centric segmental units being stackable to replace a damaged portion of a spine so that a first carbon fiber spinal fusion cage of one of the disc-centric segmental units is configured to be positioned on the same spinal vertebral body as a second carbon fiber spinal fusion cage of another of the disc-centric segmental units;

wherein the first spinal fusion cage is configured to replace about half of the first spinal vertebral body and the second spinal fusion cage is configured to replace about half of the second spinal vertebral body.

16. The surgical implant assembly of claim 15 wherein the first and second cages are constructed of a carbon fiber mesh throughout that forms interstices within the first and second cages.

17. The surgical implant assembly of claim 15 wherein the first and second cages each define at least one channel therein for receiving a screw.

18. The surgical implant assembly of claim 15 wherein the first and second cages each define an inner surface adjacent the spinal disc replacement prosthesis and an outer surface, and wherein the outer surfaces each define ridges thereon.

19. The surgical implant assembly of claim 18 wherein the first and second cages each define a groove in a portion of the circumference of the outer surface thereof to prevent posterior migration of the surgical implant assembly.

20. The surgical implant assembly of claim 15 wherein the two adjustably compartments for receiving fluid are filled with a silicone-gel fluid.

21. The surgical implant assembly of claim 15 wherein the two adjustably compartments for receiving fluid each have a port within the spinal disc replacement prosthesis through which each compartment receives fluid.

22. The surgical implant assembly of claim 15 wherein the first and second cages are affixed to the spinal disc prosthesis by an adhesive.

23. The surgical implant assembly of claim 15 wherein the surgical implant assembly is securable to the first and second spinal vertebral bodies at each respective end of the surgical implant assembly by a screw plate and one or more screws.

24. The surgical implant assembly of claim 15 comprising two or more of the disc-centric segmental units secured together in a stack to replace a damaged portion of a spine.

25. The surgical implant assembly of claim 15 wherein the first and second spinal vertebral bodies are selected from the group consisting of cervical, thoracic, and lumbar vertebrae.

26. The surgical implant assembly of claim 1 wherein the surgical implant assembly of first and second carbon fiber spinal fusion cages and a spinal disc replacement prosthesis is preassembled before installation into a spine segment.

27. The surgical implant assembly of claim 1 wherein each compartment for receiving fluid comprises an infusion tube for providing fluid to the respective compartment with the infusion tube for the posterior compartment passing through the anterior compartment.

28. The surgical implant assembly of claim 15 wherein the surgical implant assembly of first and second carbon fiber spinal fusion cages and a spinal disc replacement prosthesis is preassembled before installation into a spine segment.

29. The surgical implant assembly of claim 15 wherein each compartment for receiving fluid comprises an infusion tube for providing fluid to the respective compartment with the infusion tube for the posterior compartment passing through the anterior compartment.

30. The surgical implant assembly of claim 1 wherein the first and second spinal fusion cages each define an inner surface adjacent the spinal disc replacement prosthesis and an outer surface, wherein the outer surface of each cage is configured to engage a hemi-vertebral body or an outer surface of a second carbon fiber spinal fusion cage of another of the disc-centric segmental units.

31. The surgical implant assembly of claim 30 wherein the outer surfaces of the first and second spinal fusion cages each define ridges thereon configured to engage a hemi-vertebral body or ridges on an outer surface of a different disc-centric segmental unit.

32. The surgical implant assembly of claim 1 wherein a first spinal fusion cage of one of the disc-centric segmental units is configured to be positioned on the same spinal vertebral body as a second spinal fusion cage of another of the disc-centric segmental units.

33. The surgical implant assembly of claim 15 wherein the first and second carbon fiber spinal fusion cages each define an inner surface adjacent the spinal disc replacement prosthesis and an outer surface, wherein the outer surface of each cage is configured to engage a hemi-vertebral body or an outer surface of a second carbon fiber spinal fusion cage of another of the disc-centric segmental units.

34. The surgical implant assembly of claim 33 wherein the outer surfaces of the first and second cages each define ridges thereon configured to engage a hemi-vertebral body or ridges on an outer surface of a different disc-centric segmental unit.

* * * * *